United States Patent
Alexis (10) Patent No.: US 6,607,753 B2
(45) Date of Patent: Aug. 19, 2003

(54) NATURAL, ANTI-BACTERIAL, ANTI-VIRUS, ANTI-HERPES CREAM

(75) Inventor: Brian Alexis, 1250 Chelsea Ave., #E, Santa Monica, CA (US) 90404

(73) Assignee: Brian Alexis, Santa Monica, CA (US)

( * ) Notice: Subject to any disclaimer, the term of this patent is extended or adjusted under 35 U.S.C. 154(b) by 19 days.

(21) Appl. No.: 10/016,085

(22) Filed: Dec. 12, 2001

(65) Prior Publication Data

US 2002/0082780 A1 Jun. 27, 2002

Related U.S. Application Data

(63) Continuation-in-part of application No. 09/373,812, filed on Aug. 13, 1999, now Pat. No. 6,343,258.

(51) Int. Cl.$^7$ .............................................. A61K 35/78
(52) U.S. Cl. ........................................................ 424/725
(58) Field of Search ............................................ 424/725

(56) References Cited

U.S. PATENT DOCUMENTS

| | | | |
|---|---|---|---|
| 4,774,229 A | 9/1988 | Jordan | 514/25 |
| 5,437,866 A | 8/1995 | Sun | 424/741 |
| 5,466,452 A | 11/1995 | Whittle | 424/750 |
| 5,591,836 A | 1/1997 | Mazur et al. | 536/6.1 |
| 5,607,693 A | 3/1997 | Bonte et al. | 424/450 |
| 5,683,698 A | 11/1997 | Chavili et al. | 424/756 |
| 5,703,052 A | 12/1997 | Deninno et al. | 514/26 |
| 5,760,009 A | 6/1998 | Allen et al. | 514/26 |
| 5,906,825 A | 5/1999 | Seabrook, Jr. et al. | 424/404 |
| 5,908,628 A | 6/1999 | Hou | 424/735 |

FOREIGN PATENT DOCUMENTS

| JP | 403190809 A | 8/1991 | 424/195.1 |
|---|---|---|---|

OTHER PUBLICATIONS

Tomowa et al. Steroidsaponin Und Steroidsapogenine ; Planta medica, vol.34, (1978) pp. 188–191, English Abstract.*

Wilkins et al. Photosensitivyty in South Africa. IX. Structure Elucidation of a Beta–Glucosidase–Treated Saponin from Tribulus Terrestris. . ., Onderstepoort, J. of Vet. Research, 63:3.*

Gupta et al. Review on Phytochemical and Pharmacological Aspects of Tribulus Terrestris Linn Indian Drugs 34(B) p. 422–424 Feb. 22, 1997.

Hoffman, D. The Herbal Handbook pp. 201–211 1987.

Pharmacokinetic Studies of Tribestan [online] [retrieved on Mar. 12, 2002] Retrieved from the Internet: <URL: http://www.tribestan.com Brief product description regarding Fenusterols™ [online] [retrieved on Mar. 12, 2002] Retrieved from the Internet: <URL: http://www.sabinsa.com.

* cited by examiner

Primary Examiner—Jon P. Weber
Assistant Examiner—Patricia D Patten
(74) Attorney, Agent, or Firm—Cislo & Thomas LLP (57) ABSTRACT

Therapeutic compositions made from the herb *Tribulus terrestris* and methods of making and using the same are provided. The therapeutic compositions include an enriched extract having an increased spirostanol saponin content that is prepared from the harvested *Tribulus terrestris* L. The enriched extract is prepared using discrete hydrolysis, separation and enrichment steps. The resulting therapeutic may be combined with a cream base and is useful for treating bacterial, fungal, and viral infections, particularly gynecologic infections. This product was also found to be very successful in suppository form for the treatment of vulvo-vaginal, vulvo-hemorrhoidal and colonic conditions.

4 Claims, 9 Drawing Sheets

Figure 1. Complaint of vulvo-vaginitis symptoms evaluated by importance

Figure 2. Evaluation of symptoms after first treatment

Percent reduction in symptoms

| SYMPTOMS | Day 1 % | Day 3-5 % | Day 7 % |
|---|---|---|---|
| Leukorrhea | 71.8 | 11.4 | 2.0 |
| Pruritis | 57.9 | 2.0 | 2.0 |
| Burning | 38.1 | 2.0 | 0 |
| Edema | 22.7 | 0.8 | 0 |
| Erythema | 45.8 | 4.1 | 2.0 |

Figure 3. Evaluation of symptoms after first treatment

Figure 4. Daily patient evaluation of improvement of symptoms

Figure 5. Physician assessment of results of treatment

```
CHROMATOGRAM 5 MEMORIZED
CR501 CHROMATOPAC                    FILE         0
CHANNEL NO. 1                        METHOD       0424
SAMPLE NO. 0                         SAMPLE WT    100
REPORT NO. 76
```

| PEAK NUMBER | TIME | AREA | MK | IDNO | CONC | NAME |
|---|---|---|---|---|---|---|
| 1 | 2.301 | 2053434 | | 1 | | |
| 2 | 2.524 | 2208158 | V | 1 | | |
| 3 | 2.861 | 1495685 | V | | | |
| 4 | 3.489 | 2191742 | 8V | | | |
| 5 | 6.167 | 622859 | V | | | |
| 6 | 7.183 | 1150069 | V | 4 | | |
| 7 | 7.859 | 1688122 | V | | | |
| 8 | 8.597 | 703429 | V | | | |
| 9 | 9.94 | 572807 | V | 5 | | |
| 10 | 10.967 | 1017776 | V | | | |
| 11 | 12.659 | 801423 | V | | | |
| 12 | 13.627 | 697001 | V | | | |
| 13 | 14.242 | 312845 | V | | | |
| 14 | 14.902 | 586059 | V | | | |
| 15 | 15.704 | 6626650 | V | 6 | | |
| 16 | 16.31 | 524594 | V | 6 | | |
| 17 | 17.147 | 621246 | V | | | |
| 18 | 17.741 | 818086 | V | | | |
| 19 | 18.713 | 605805 | V | | | |
| 20 | 19.056 | 315054 | V | | | |
| 21 | 19.671 | 717887 | V | | | |
| 22 | 20.287 | 684753 | V | | | |
| 23 | 21.282 | 2374513 | V | 7 | | |
| 24 | 22.816 | 1857069 | V | 7 | | |
| 25 | 23.498 | 1135145 | V | | | |
| 26 | 24.817 | 2397739 | V | | | |
| 27 | 25.897 | 1435988 | V | | | |
| 28 | 26.659 | 503252 | V | | | |
| 29 | 27.185 | 1212220 | V | | | |
| 30 | 28.864 | 2759425 | V | | | |
| 31 | 31.917 | 8740921 | V | | | |

```
             TOTAL    42936472                    176.6883
```

FIG. 7

SPIROSTANOL SAPONINS

FIG. 8

FUROSTANOL TYPE SAPONINS

β-GLUCOSIDASE ENZYME OR ACID HYDROLYZE

SPIROSTANOL TYPE SAPONINS

Glucoside C (I) under enzymatic hydrolysis and oxidative degradation as the furostanol Bisglucoside protodioscin(III) and spirostanol diosgenin(II), pregnenolonglicosid(IV), Glucosid(V) and Δ5,16-{regnenol-/3β/-on-/20/(VI), trace of tigogenin, glucose and ramanose.

NATURAL, ANTI-BACTERIAL, ANTI-VIRUS, ANTI-HERPES CREAM

CROSS-REFERENCES TO RELATED APPLICATIONS

This patent application is a continuation-in-part and claims priority from U.S. patent application Ser. No. 09/373,812 filed Aug. 13, 1999 now U.S. Pat. No. 6,343,258 for METHOD FOR TESTING FOR READINESS OF HARVESTING OF *TRIBULUS TERRESTRIS* L. HAVING HIGH STERIODAL SAPONIN CONTENT, which application is incorporated herein by this reference thereto.

BACKGROUND OF THE INVENTION

1. Field of the Invention

This invention relates to the field of therapeutic compounds for the treatment of diseases of the skin and mucosal tissue. In particular the present invention relates to creams, ointments, eye and ear drops made from the herb *Tribulus Terrestris* that have a high content of spirostanol-type steroidal saponins and are useful in the treatment of conditions related to viral, fungal, yeast, parasitic and bacterial infections, particularly genital, skin (including acne) and eye and ear infections.

2. Description of the Related Art

*Tribulus Terrestris*, commonly known as "Puncture Vine" or Caltrop fruit, is an herb that has been used for centuries in Europe for hormone insufficiency in men and women. It has also been used in the treatment of liver, kidney and urinary tract disease. In recent years *Tribulus Terrestris* has been touted as a dietary supplement for improving athletic performance. It has been discovered that ingestion of *Tribulus terrestris* significantly elevates the level of several hormones: Testosterone; Luteinizing Hormone; Follicle Stimulating Hormone; and Estradiol. Clinical studies on Tribulus, conducted at the Chemical Pharmaceutical Institute in Sofia, Bulgaria, showed improved reproductive functions, including increased sperm production and Testosterone levels in men. Among women, *Tribulus terrestris* L. increased the concentration of hormones including Estradiol, with Testosterone being very slightly influenced, thereby improving reproductive function, libido and ovulation.

The active components of the *Tribulus terrestris* L. plant also have a stimulating effect on the immune, sexual and reproductive systems, leading to improved muscle building, stamina and endurance. Other positive changes observed in a number of cases were a reduction in cholesterol, enhanced mood and well-being. No adverse effects to the central nervous or cardiovascular systems were noted in any of the clinical studies.

The Tribulus plant is also of interest due to the increasing clinical importance of emerging pathogens as well as drug-resistant microorganisms, which lend additional urgency to identify novel, active compounds. Currently available drugs for the treatment of fungal infections include amphotericin B (a macrolide polyene), which interacts with fungal membrane sterols, flucytosine (a fluoropyrimidine), which interferes with fungal protein and DNA biosynthesis, and a variety of azoles (e.g. ketoconazole, itraconazole, and fluconazole) that inhibit fungal membrane-sterol biosynthesis (see e.g. Alexander, B. D. et al., Drugs, 1997, 54:657–678). Although amphotericin B has a broad range of activity and is viewed as the "gold standard" of antifungal therapy, its use is limited due to infusion-related reactions and nephrotoxicity (see Alexander, B. D. et al., Drugs, 1997, 54:657–678). Flucytosine usage is also limited due to the development of resistance and its narrow spectrum of activity. Further, the widespread use of azoles is causing the emergence of clinically-resistant strains of Candida spp. (see Alexander, B. D. et al., Drugs, 1997, 54:657–678). This problem is particularly important in treating vaginal infections due to bacteria, parasitis and fungi.

Other commonly used agents in treating vaginal infections include dimethylalkybenzalkonium choloride, nonylphenololyoxyethylene or nonoxynol-9. The use of these bacteriocidal agents in vaginally inserted suppositories, creams, foams or the like, however, is also not without problems inasmuch as these agents tend to diminish or destroy the healthy bacterial flora of the vagina, and cause a tendency to develop yeast infections (candidasis). Further, many of the prior art compositions have a narrow spectrum of action in that they cover only some of the microorganisms responsible for a particular condition.

In this respect, the *Tribulus terrestris* L. plant has been a promising alternative to existing "chemical" antimicrobials. *Tribulus terrestris* L. contains saponins, which in plants, are formed from a sapogenin core linked with a sugar. The sapogenin, or glycoside, may be a steroid or a triterpene and the sugar moiety may be glucose, galactose, a pentose or a methyl pentose. Samples of *Tribulus terrestris* L. extract prepared according to the invention disclosed herein have been found to include tigogenine, diosgenin (a steroid sapogenin), desoxydiosgenin astragalin, kampferol (a flavanoid), dioscin (a furostanol that converts to diosgenin and glucose under hydrolysis), protodioscin (a furostanol), harmine (a bioflavanoide), linoleic acid, galactoolysaccharide, protogracillin and kampferol biofavanoide compounds. As with many secondary plant compounds, the concentration of saponins within a plant will vary depending upon the identity of the plant, the source of saponin within the plant (e.g. seed, fruit, leaves) and the conditions under which the plant is grown. The method of extraction will also affect the concentration of saponins. Generally, however, saponins are present in conventional extracts at about 15 to 25 percent by weight and average at about 20% by weight.

Saponins are also found in soybeans, alfalfa, and ginseng have been studied extensively for their effect of lowering cholesterol. For example, U.S. Pat. No. 4,242,502 issued to Malinow et al (1980) relates to the use of saponins to inhibit cholesterol absorption. According to this reference, modification of the oligosaccharide portion of the saponin by hydrolysis under mild acid conditions affects the saponins' ability to affect cholesterol absorption. More particularly, when the sugar moiety of the saponin molecule is removed, i.e., the glycosidic linkage is cleaved, it was found that the cholesterol is no longer removed. Therefore, hyrolysis of saponin in the stomach or intestine is an important factor in considering the efficacy of saponin-containing therapeutic compound, for example, in the treatment of hypercholesterolemia. To this effect, U.S. Pat. No. 5,760,009 (Allen et al., 1998) discloses a crystalline monohydrate of a spirostanol glycoside that is not degraded in the digestive system and is useful for the control of hypercholesterolemia or atheroscerosis. Topical application of saponins also presents special consideration for therapeutic efficacy since not all saponins are topically bio-active.

The steriodal saponins found in the herb *Tribulus terrestris* are two types; furostanols and spirostanols. Furostanol steroidal saponins from *Tribulus terrestris* L. are not topically bio-active and must be first converted to spirostanols to become bio-active, for example, via enzyme hydrolysis. The instant invention discloses the use of *Tribulus terresteris* L. compositions having a high spirostanol saponin content useful in treating fungal, bacterial viral and parasitic infections and methods for making the same.

SUMMARY OF THE INVENTION

The present invention includes pharmacologic compositions derived from the herb *Tribulus Terrestris* L. that have a high content of spirostanol-type steroidal saponins and/or balance the ratio of furostanol to spirostanol-type saponins in the resulting composition. The compositions may be used topically, orally and on mucosal tissues and exhibit a strong anti-bacterial, anti-inflammation, anti-viral, and anti-herpes effect. They are highly useful in treating vaginal infections, skin disorders and viral infections such as herpes simplex I and herpes simplex II, and in some cases may block cancer cells from growing.

The compositions disclosed herein may be combined with ingredients known in the art to provide creams, ointments, and eye and eardrops. For example, the present invention discloses a cream made from *Tribulus Terrestris* L. that has a very strong anti-bacterial, anti-inflammation, anti-virus, anti-herpes effect, represents a great improvement in the fields of dermatology and gynecology and satisfies a long felt need of dermatologists and gynecologists. Additionally, the compounds and methods disclosed herein are useful in treating cervical wounds, cervical erosion, diabetic wounds, Burger disease, phlebitis, rashes, skin burning, varicose veins and broken split skin.

The compositions disclosed herein are prepared using methods comprising isolation, enzyme hydrolysis, and enrichment steps to optimize the spirostanol content of the resulting therapeutic composition. To prepare a composition having optimal spirostanol content, a first extract is prepared by first carrying out, preferably, a low temperature water/alcohol extraction of the *Tribulus Terrestris* L. plant material. A number of factors are critical in preparation of the *Tribulus Terrestris* L raw material and the extraction procedure. These include: time of harvesting the *Tribulus terrestris* L., part of the herb used, specific geographic area where the herb is gathered, the method of harvesting, and low temperature drying. Adherence to these factors guarantees high steroidal saponin, sapogenin and sterol content of the raw material used for making the extracts and resulting pharmacologic compositions.

For example, harvesting *Tribulus terrestris* L. from southern Bulgaria between approximately July first and August fifteenth ensures that the harvested *Tribulus terrestris* L. has a high saponin content. A sample of the crop to be harvested can be tested prior to harvesting according to the method disclosed in U.S. patent application Ser. No. 09/373,812 to further ensure that the *Tribulus terrestris* L. has optimal saponin content. Alternately, the crop to be harvested can be tested prior to harvesting according to the method disclosed in U.S. patent application Ser. No. 09/373,812, but using a general ratio of one part water to two and one half parts of dried raw plant material.

A water/alcohol extraction of the herb *Tribulus Terrestris* L may then be performed and the resulting extract concentrated with a vacuum evaporator. To prepare a highly bio-active extract of *Tribulus terrestris* L., spirostanol steroidal saponin, sterol and bio-flavanoides, are isolated from a first *Tribulus terrestris* L. extract and are blended with a second *Tribulus terrestris* L. extract. More particularly, in a first step, the first extract is treated to hydrolyze furostanols contained in the extract to convert them into spirostanols. In a second step, the spirostanols in the first extract are isolated and added to a second prepared *Tribulus terrestris* L. extract. The resulting composition may be mixed with ingredients known in the art to form a cream, liquid or ointment and has been found to be very successful in suppository form for the treatment of bacterial, fungal, yeast, parasitic and bacterial infections.

OBJECTS OF THE INVENTION

An appreciation of the other aims and objectives of the present invention and an understanding of it may be achieved by referring to the accompanying drawings and description of a preferred embodiment.

BRIEF DESCRIPTION OF THE DRAWINGS

FIGS. 6-1 and 6-2 represent High Pressure Liquid Chromatography data from a *Tribulus Terrestris* L. sample as prepared by the methods disclosed herein showing the protodioscine peak.

DESCRIPTION OF THE PREFERRED EMBODIMENT(S)

The detailed description set forth below in connection with the appended drawings is intended as a description of presently preferred embodiments of the invention and is not intended to represent the only forms in which the present invention may be constructed and/or utilized. The description sets forth the functions and the sequence of steps for constructing and operating the invention in connection with the illustrated embodiments. However, it is to be understood that the same or equivalent functions and sequences may be accomplished by different embodiments that are also intended to be encompassed within the spirit and scope of the invention.

The herb *Tribulus Terrestris* L. is preferably harvested from the southern part of Bulgaria where high concentration of steroidal saponins, sapogenins and sterols in the herb has been confirmed by years of analysis. Preferably, the leaves, fruits and stems of the plant are used, without addition of the underground portions of the plant. Prior to harvesting, a sample of the crop is preferably first tested for readiness of harvesting by a quick qualitative analysis of the steroidal saponin, sapogenin and sterol content of the plant. For testing, an approximately 500 mg of harvested and dried (at a temperature of 45 C.) plant material (leaves, fruits and stems) of *Tribulus Terrestris* L is preferably used. The dried sample is preferably blended for approximately 15 minutes in a container with approximately 200 ml water. Upon blending, if the white foam level of the saponins is about 1.5 higher than the water level, the plant is ready for harvesting. Once activity of steroidal saponins is confirmed, the harvesting process is preferably completed within one week to ensure optimal levels of steroidal saponins in the harvested plants.

Alternately, testing for optimal harvesting time of a sample of *Tribulus terrestris* L. may be carried out by performing the testing procedure above, but using dried *Tribulus terrestris* L. and water at a ratio of 2.5 parts dried plant material to 1.0 part water and blending for approximately fifteen (15) minutes. The blending time may be increased as the sample of plant material becomes greater than 500 mg. As in the first method, optimal levels of steroidal saponins in the sample can be confirmed by ascertaining whether the white foam level of the saponins is about 1.5 higher than the water level, in which case the plant is ready for harvesting. The optimal time of harvesting *Tribulus terrestris* L. in Bulgaria is usually between July 1 and July 30 or, depending on the weather conditions, to as late as August 15.

Once the plant has been harvested it is preferably stored in a dry place or dried immediately. If the herb is dried, it is preferably done at a low temperature (40° C.) in an oven or at room temperature in a dry, very well ventilated facility. In order to keep the activity of the steroidal saponins in the raw material high, the moisture content is preferably less than 10%. Once harvested, a high speed shredder and mixer may be used to pulverize the plant material to release steroidal saponins and sapogenins from the plant tissue. Preferably, a mixture of leaves, fruit and stems is cut or shredded to approximately 0.1 mm to 10 mm. The plant material is then ready for the extraction step.

To prepare the *Tribulus terrestris* L. extract, the preferably shredded plant material is first mixed with water. A ratio of approximately 300 ml of deionized water for each 1 g of plant material is preferable, but other ratios may be used. For example, 300 ml deionized (DI) water may be added to 1 g of plant material and blended in a container for about 15 minutes to form a mixture. It is preferable that sufficient speed be used to create a substantial vortex in the mixture. Next, a solvent is added to the mixture, preferably in the ratio of one part solvent to two parts of mixture. For example, about 150 ml of a solvent such as ethyl alcohol may be added to 300 ml of the mixture, mixed, and left for 48 hours, after which the mixture is filtered. The solvent is then distilled off and the water extract concentrated with a vacuum evaporator to about 1 ml for each g of starting mixture.

Figure 8:
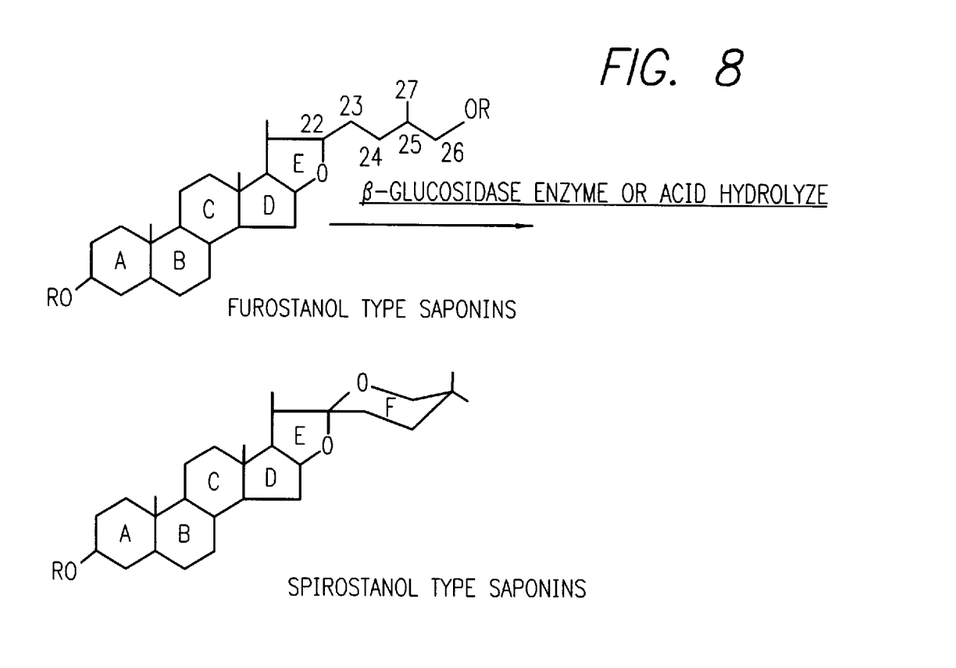
FIG. 8 illustrates enzyme hydrolysis of furostanol saponins by B-Glucosidase or acid hydrolysis to from spirostanol saponins.
Figure 9:
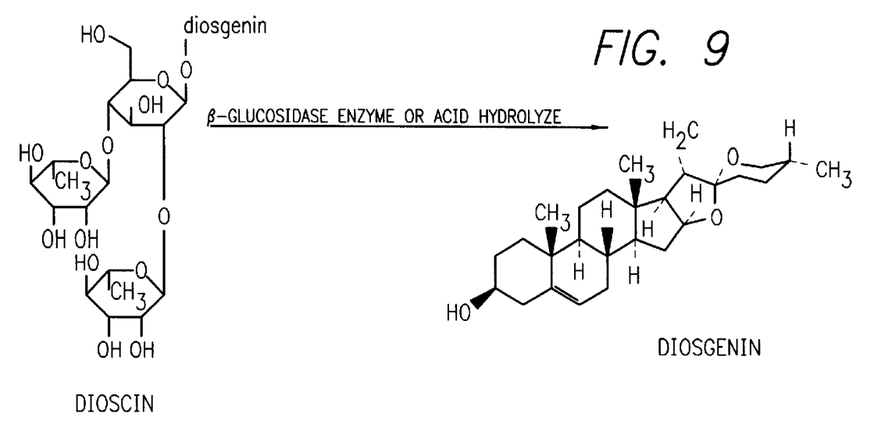
FIG. 9 illustrates hydrolysis of Dioscin to Diosgenin.
Figure 10:
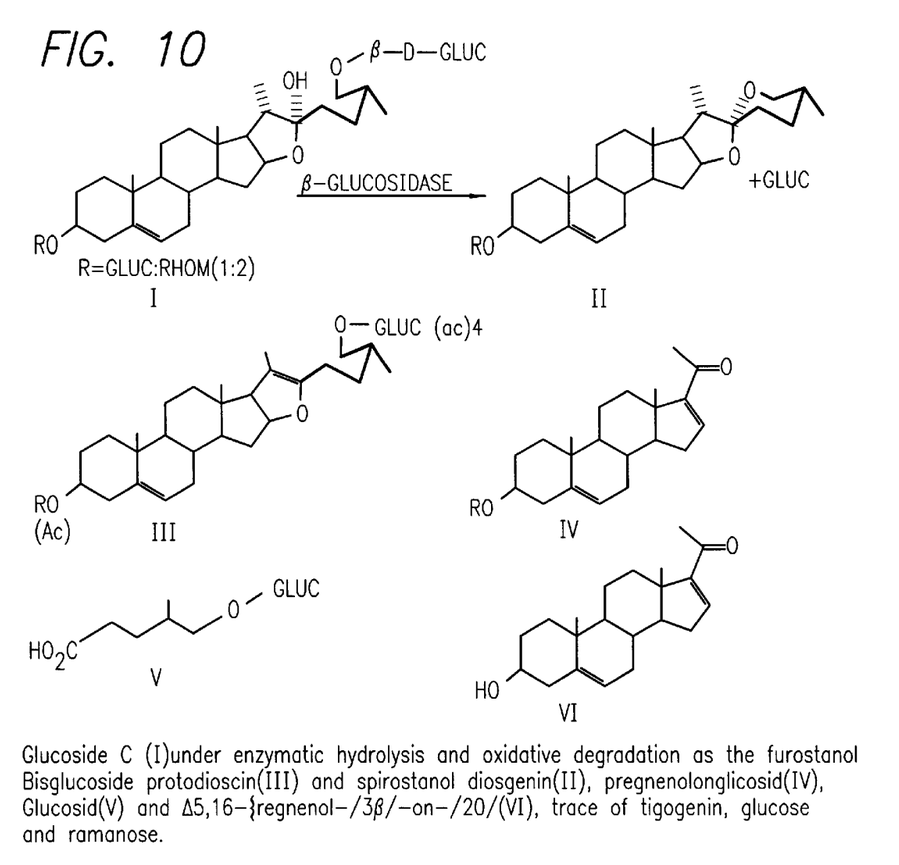
FIG. 10 illustrates hydrolysis of furostanols to spirostanols.
Figure 61:
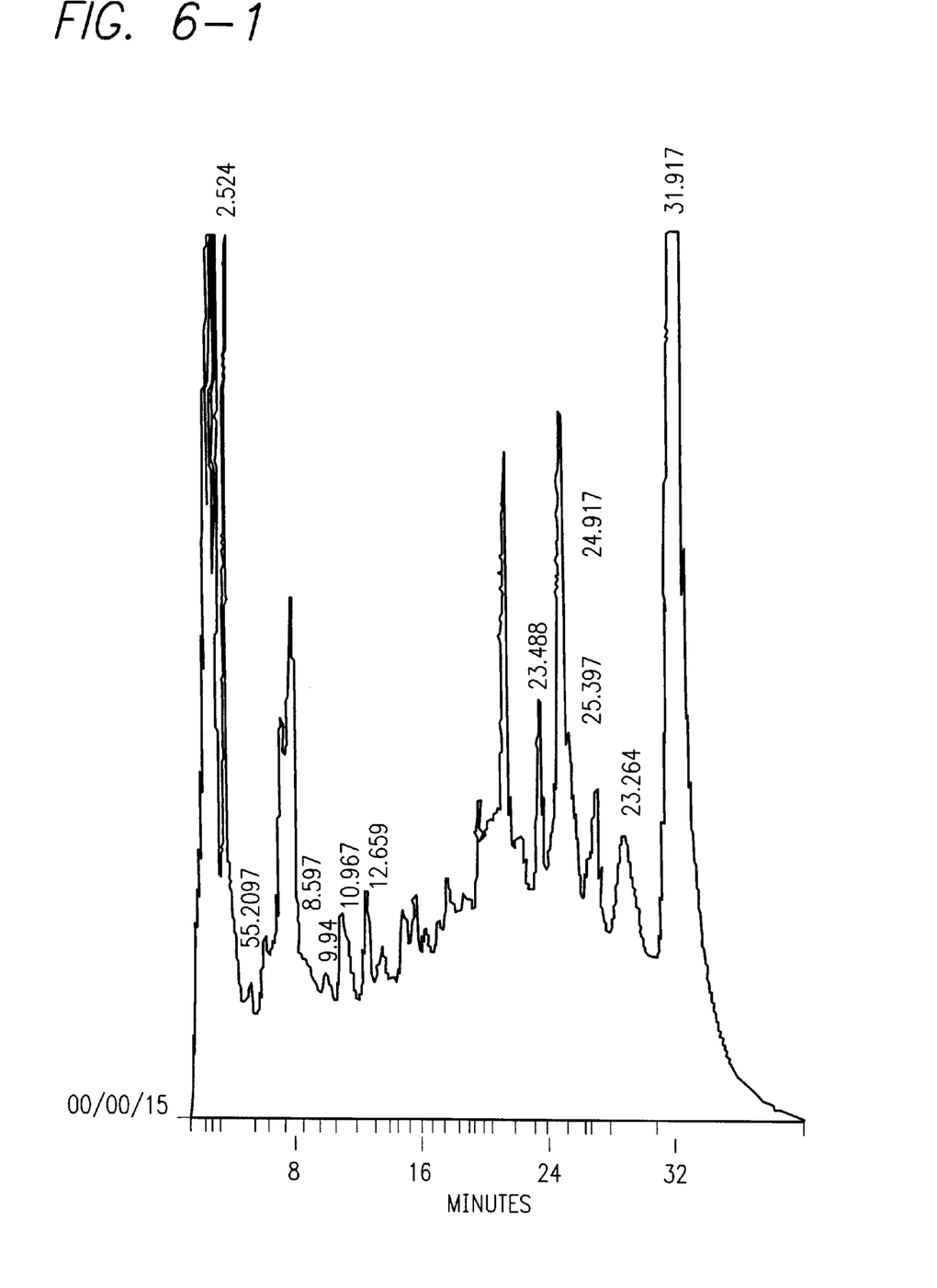
Figure 62:
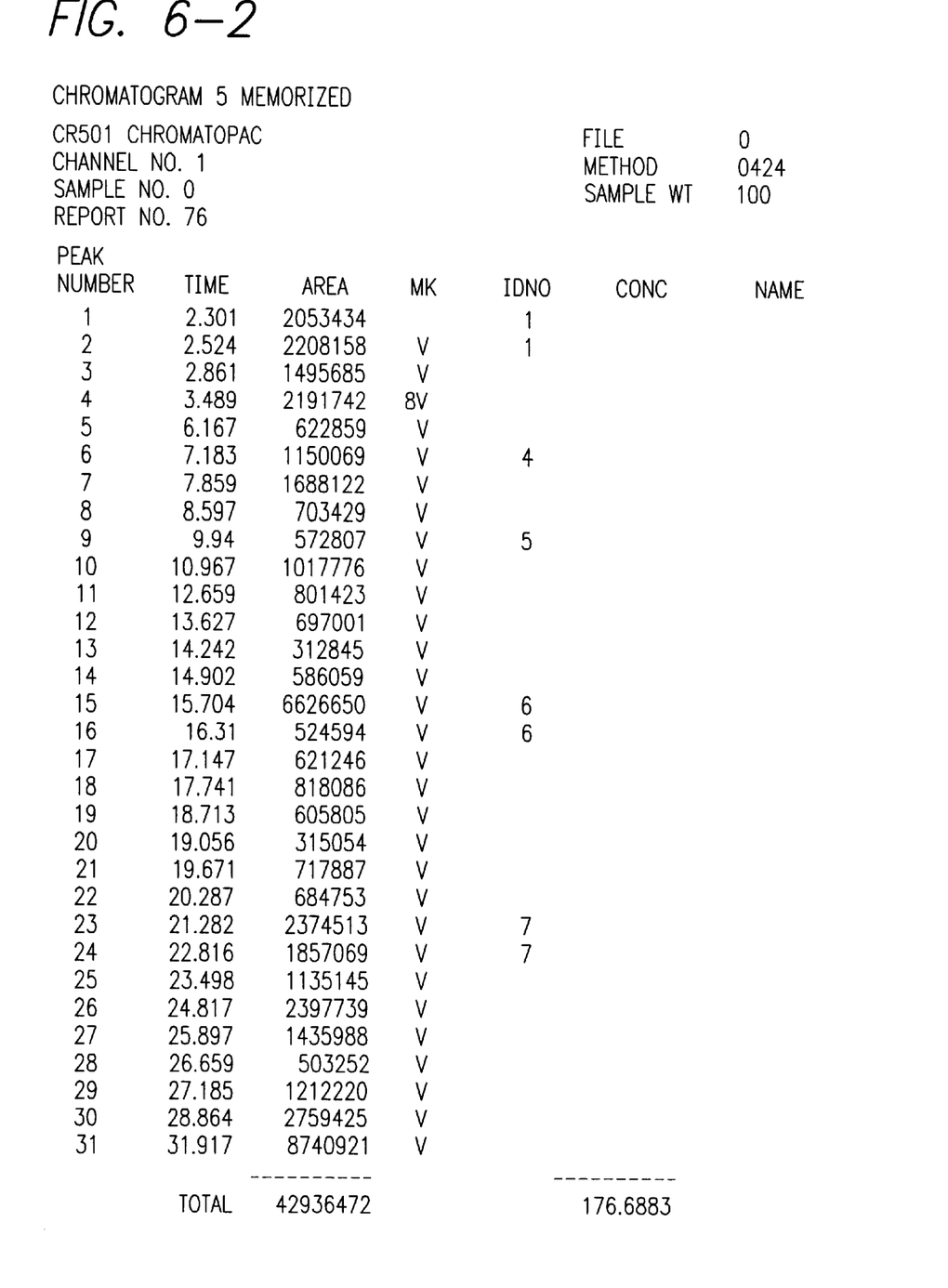

Next, the first extract is next treated to optimize the spirostanol content of the resulting composition. This is accomplished by initially subjecting the first extract to a hydrolysis step, which is preferably an enzymatic hydrolysis, but may also be acid hydrolysis. The hydrolysis step cleaves the furostanols contained in the first extract, as illustrated in FIG. 8, to form bio-active spirostanols. The spirostanols are then separated and isolated from the first extract. This may be accomplished by using chromatographic columns packed with silica gel or other packed material to separate out spirostanols by size of the molecule using a mobile phase (organic solvent: alcohol: water) for each solvent quantity ratio 1:100, wherein the first fractions to 10 are separated and added to the next fresh solutions. The spirostanol saponins are contained in the next 20 to 100 fractions. All fractions are added together, dried in a vacuum evaporator and purified two times with crystallization. The isolated spirostanols are then added a second dried Tribulus extract that is prepared by, for example, the ethyl alcohol extraction noted above, and blended. Alternately, spirostanols may be isolated by way of micro ultra filtration, which separates out all active ingredients of the *Tribulus terrestris* extract by size of the molecule. The isolated spirostanols are then purified with crystallization and added to a second dry extract to form an enriched extract. Using the method disclosed above, the concentration of spirostanol saponins in the enriched dry extract may be from 0.1to about 100%.

The enriched extract may be then be mixed with agents known in the art to form, for example, a cream base, ointment or liquid to an enriched extract concentration of about 1% to about 50% of the final composition, depending upon the therapeutical application. Any cream base used for dermatological uses can be used. Alternatively, the extract may be mixed with glycerin or paraffin to make a suppository form. Conventional thickening agents, such as hydroxypropylmethylcellulose, may be used to adjust the viscosity to the degree best adapted to the form of the composition (solution, cream, gel etc.). Generally speaking, the object of the present invention can also be attained by a vaginal cream, foam, ointment, or suppository. For advantageous application, the composition in accordance with the invention can contain in addition a buffering agent such as hydrochloric acid in order to be able to adjust the pH to about 4.7, which aids in maintaining healthy vaginal flora.

EXAMPLE I

Extraction of the plant material may be accomplished by the method of the following example. Shred a mixture of leaves, fruit and stems of *Tribulus Terrestris* to a size of 0.1 to 10 mm in a shredder. For each 1 g of mixture, add about 300 ml deionized (DI) water and extract for about 15 min in a blender. Sufficient speed should be used to create a substantial vortex. Add about 150 ml ethyl alcohol, mix, leave for 48 hours and then filter. Distill off the ethyl alcohol then concentrate the water extract with a vacuum evaporator to about 1 ml for each g of starting mixture. Finally, mix with a cream base to a concentration of 5% and 7.5% *Tribulus Terrestris* L concentrated water extract. Any cream base used for dermatological uses can be used. Alternatively, mix with glycerin or paraffin to make into a suppository form.

EXAMPLE II

Creams made as described above with 5% and 7.5% *Tribulus Terrestris* L enriched extract were used for local treatment in 275 women with vulvo-vaginitis. A physician carried out the treatment after obtaining samples from the vagina, cervix and vulva. In most cases the condition was classified as candidiasis. Application of the creams was done after the confirmation of the diagnosis through microbiological testing. Quick improvement of the symptoms of the vulva was noted even on the first day of the application of the cream.

The treatment had very good acceptance according to the opinion of the patients as well as their physicians. Vaginal antiseptic creams are preparations for treatment of local problems of the vulva in the region of the vulvo-vagina. The epithelia of the vagina is an effective barrier against infection, however, at the same time it is a propitious environment for the development of protective flora and can permit development of numerous pathogenic microorganisms.

Their action has a maximal effectiveness in pH 4–5.6, which precisely the physiologic value of pH in the vagina as well as the pathological values of pH there.

Patients

The investigation was conducted with women above 16 years of age with vulvo-vaginitis with various etiology (bacteria, fungi, parasites, etc.) with at least two of the following symptoms:

Leukorrhea

Pruritis

Burning

Edema

Erythema

Patients with the associated symptoms of the upper genitalia were excluded from the study. Two hundred and seventy-five (275) patients were followed for a period of 9 months. The patients' ages varied from 16 to 62 years with a mean age of 32. More than 90% were younger than 45 years. In 71.6% of the cases the patients were using contraception, most often oral (44.40%) and intra-uterine (25.1).

Lower genital pathology (vulvo-vaginitis) was the cause for consultation in 63.3% of the cases and 29.1% were regular patients in whom vulvo-vaginitis was diagnosed. A tendency of recurrence is seen in approximately 40.7% of women diagnosed with vulvo-vaginitis.

The initial diagnosis during investigation was:

candidiasis—83.9% trichomonasis—7.3% bacterial vaginosis—4.0%

*chlamidia cervicitis*—0.8% herpes—0.8%

*e-coli*—0.8% condyloma—0.8% infected ectopia—0.8% abscess of the left labia—0.8% diagnosis of mycosis was confirmed in 76% of the cases and rejected in 24%.

The treatment with the antiseptic creams was carried out by applying the cream of this invention to the whole vagina, including the cervix. Investigation consisted of three obligatory check-ups. The first check-up was done at the beginning of treatment (first day of the check-up) thorough clinical gynecologic check-up, obligatory microbiological investigation and competent endocervical sampling. The second check up (second endocervical sample) was carried out on the seventh day. The third check-up was done on the fourteenth day of the treatment. In cases of regression, without complete healing on the fourteenth day, a new application of the cream to the vagina was done.

The total effectiveness of the treatment was evaluated on the basis of the development of the clinical symptoms, which motivated the person to be included in the investigation: leukorrhea, pruritus, burning, edema and erythema. Each clinical symptom was evaluated on a degree from 0 to 3, according to the intensity during each check-up:

0—lack

1—of low importance

2—important

3—very important

The following of all symptoms during the check-up allowed following the clinical development of the process.

Each undesirable effect was noted on the evaluation sheet. It was presented during the second check-up. The sheet required the patient to evaluate the acceptance of the treatment as well as the development of the symptoms, general treatment and the vaginal cream in particular.

Figure 1:
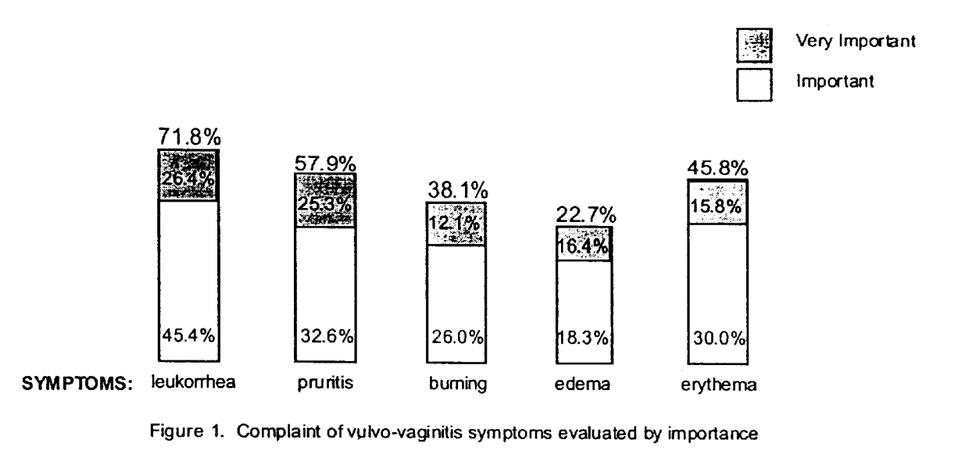
FIG. 1 is a graph showing the importance of vulvo-vaginitis symptoms.
Figure 2:
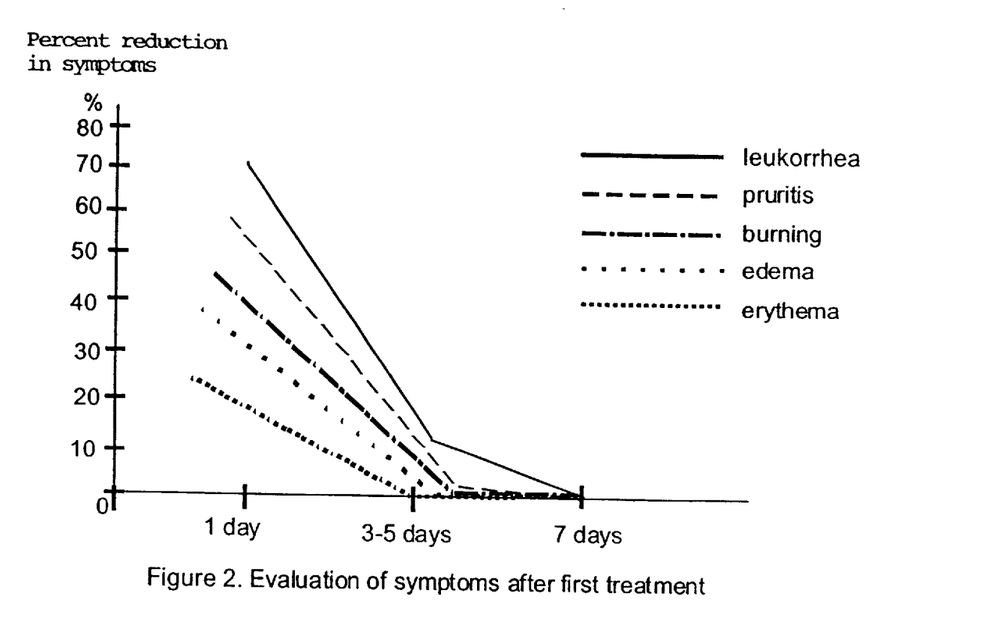
FIG. 2 is a graph showing how various symptoms improve with treatment.
Figure 3:
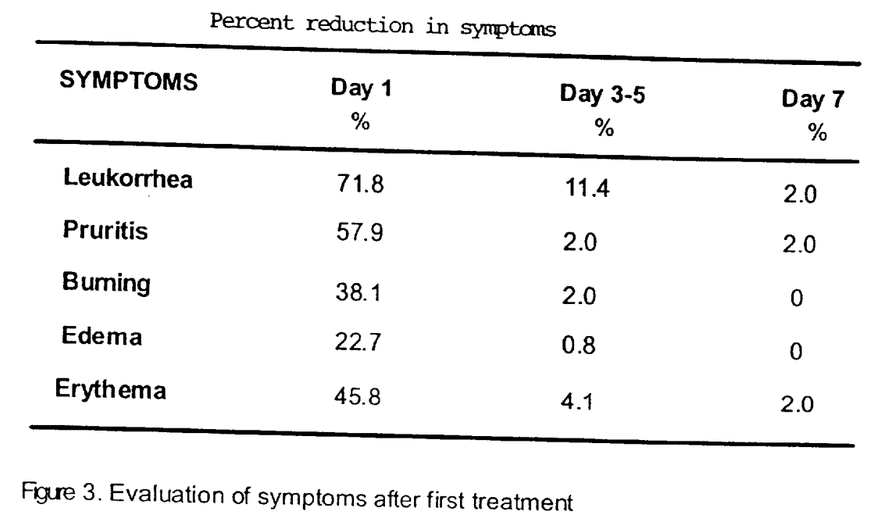
FIG. 3 is a chart of the data used in preparation of FIG. 2.
Figure 4:
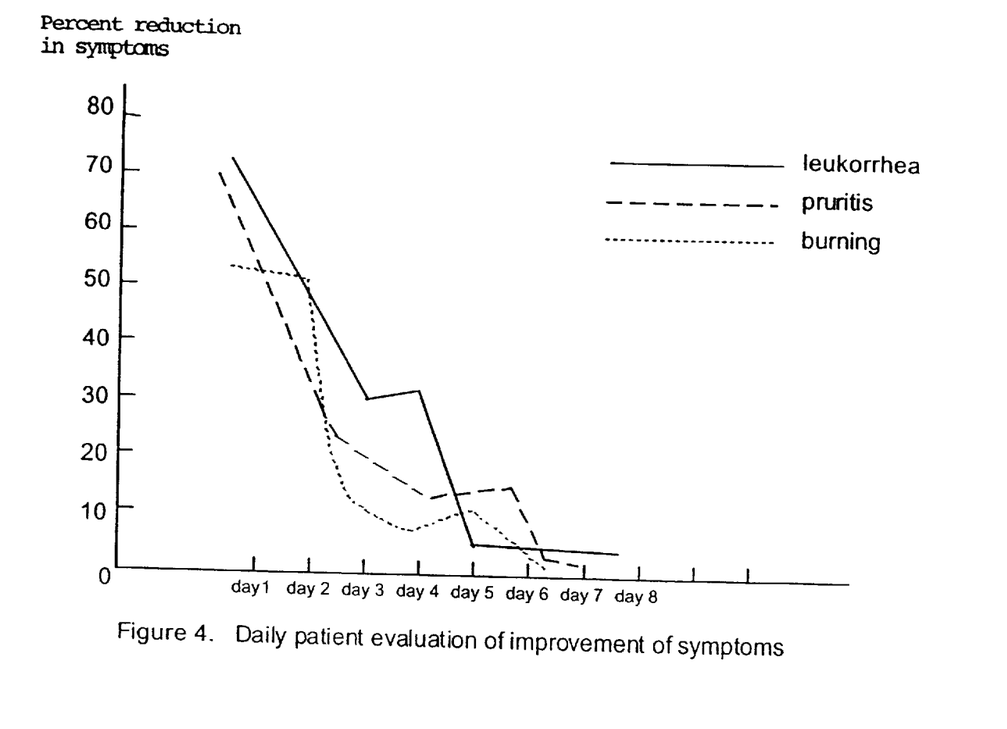
FIG. 4 is a graph showing improvement in various symptoms.

The majority of important symptoms (No. 2 and 3) disappeared on the second check-up on day 7 of the treatment (FIGS. 2 and 3). Results were evaluated on day 3, day 5 and day 7. These results were very significant. In 93of the cases the patients were considered healed. That is the total result is less or equal on day 3, 5 and 7. Development of the symptoms was evaluated each day by the patient up to the $7^{th}$ day of the treatment, which allowed for assessment of the speed of improvement of the leukorrhea, pruritus and burning. Symptoms of the leukorrhea, pruritus and burning had almost disappeared by the $3^{rd}$–$4^{th}$ day. See FIG. 4.

Figure 5:
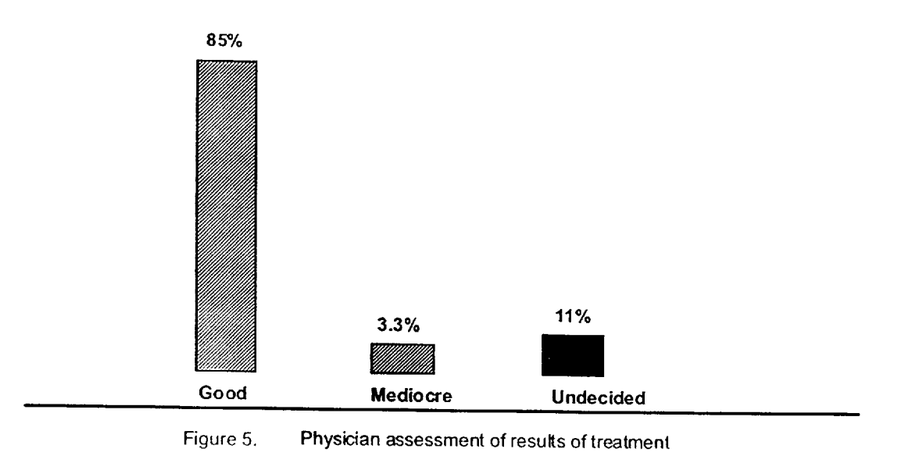
FIG. 5 is a bar chart showing physician assessment of results of treatment.
Figure 7:
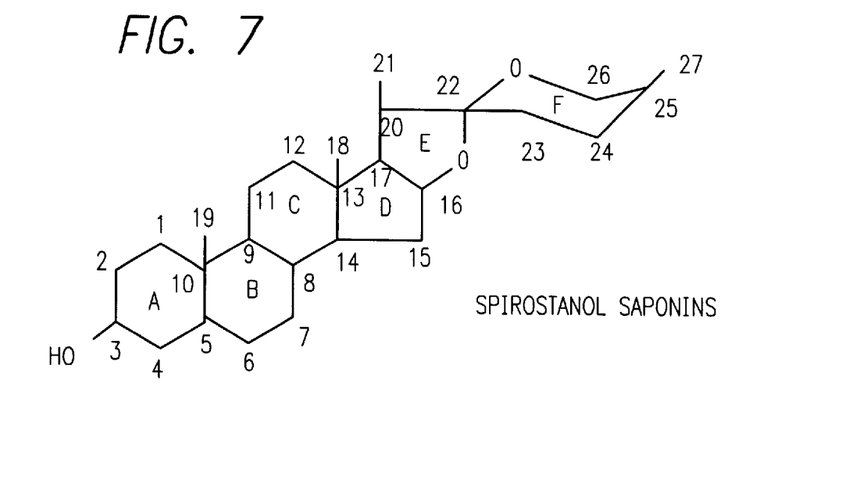
FIG. 7 illustrates the general formula for a spirostanol.

The cream was very well accepted by 9 out of 10 patients. Acceptance was perceived as good in 85% of the cases and mediocre in 3.3% (FIG. 5). Subjectively, acceptance was considered good by 98.4% of the patients and bad by 2.4%.

Side effects reported were:

itching slight irritation in the beginning slight redness in the beginning (This investigation was carried out in French Department Specialise Gynecologie Obstetrique Sofia, Bulgaria by Dr. B. Kirtchev.)

EXAMPLE III

Clinical Investigation with *Tribulus terrestris* L. Acne Cream

37 Patients with acne symptoms were treated with a cream-based composition containing an enriched *Tribulus terrestris* L. extract prepared according to the method disclosed herein. The cream was prepared by dissolving the dry extract of steroidal saponins enriched with spirostanol steroidal saponins, as disclosed herein, in purified water. The mixture was then heated to 40–50° C. and added to the cream base, which is at a temperature of 60–65° C. The mixture is mixed continuously until the cream is homogenized. The concentration of dry enriched extract in the cream may be from approximately 0.1to about 50%, depending upon the therapeutic application. The concentration of the enriched spirostanol steroidal saponins in the dry extract, which contains steroidal saponins, sterols, and flavanoides isolated from the *Tribulus terrestris* L. plant is preferably from about 0.1% to about 100% of the dry extract, depending upon the therapeutic application. An ointment can also be prepared, preferably at a concentration of from about 0.1% to about 50% of the enriched dry extract, and a suitable base.

EXAMPLE IV

Preparation of Therapeutic Liquid for Eye and Ear Drops

Liquid Composition for Eye Infections

Dissolve 1% to 5% of the enriched extract prepared according to the method disclosed herein in sterile purified water. The enriched extract preferably has a spirostanol saponin content of about 0.1% to about 100%, and may contain other sterols and bioflavanoides. Sodium citrate, citric acid, tyoxapol, edentate sodium may be added.

Liquid Composition for Ear Infections

Dissolve 1% to 50% of the enriched extract prepared according to the method disclosed herein in sterile purified water. The enriched extract preferably has a spirostanol saponin content of about 0.1% to about 100%, and may contain other sterols and bioflavanoides. Sodium citrate, citric acid, tyoxapol, edentate sodium may be added.

The invention has been described with reference to particular embodiments. Other modifications and enhancements can be made without departing from the spirit and scope of the claims that follow.

What is claimed is:

1. A method to prepare an anti-bacterial, anti-viral, anti-herpes anti-fungal topical medication comprising:
   (a) preparing an aqueous first extract of *Tribulus terrestris* L;
   (b) treating the first extract to convert furostanol saponin compounds contained therein to spirostanol compounds;
   (c) isolating the spirostanol compounds from the first extract;
   (d) a adding the isolated spirostanol compounds to a second *Tribulus terrestris* L. extract to form an enriched extract; and
   (e) adding the enriched extract to a base suitable for topical or mucosal application to form the topical medication.

2. The method of claim 1 wherein the furostanol saponin compounds in the first extract are hydrolyzed by a method select from the group consisting of enzymatic hydrolysis and acid hydrolysis.

3. The method of claim 2 wherein the furostanol saponin compounds in the first extract are hydrolyzed by beta-glucosidase.

4. The method of claim 2, wherein the furostanol saponin compounds in the first extract comprise protodioscine and the spirostanol compounds comprise diosgenin.

* * * * *